US009173858B2

(12) United States Patent
Leaute-Labreze et al.

(10) Patent No.: US 9,173,858 B2
(45) Date of Patent: *Nov. 3, 2015

(54) USE OF A BETA BLOCKER FOR THE MANUFACTURE OF A MEDICAMENT FOR THE TREATMENT OF HEMANGIOMAS

(71) Applicant: UNIVERSITE VICTOR SEGALEN-BORDEAUX 2, Bordeaux Cedex (FR)

(72) Inventors: Christine Leaute-Labreze, Le Haillan (FR); Eric Dumas De La Roque, Villenave d'Ornon (FR); Alain Taieb, Bordeaux (FR); Jean-Benoit Thambo, Bordeaux (FR)

(73) Assignees: Universite de Bordeaux, Bordeaux (FR); Centre Hospitalier Universitaire de Bordeaux, Talence (FR)

( * ) Notice: Subject to any disclaimer, the term of this patent is extended or adjusted under 35 U.S.C. 154(b) by 213 days.

This patent is subject to a terminal disclaimer.

(21) Appl. No.: 13/678,902

(22) Filed: Nov. 16, 2012

(65) Prior Publication Data
US 2013/0072551 A1  Mar. 21, 2013

Related U.S. Application Data

(63) Continuation of application No. 12/599,266, filed as application No. PCT/IB2008/002746 on Oct. 16, 2008, now Pat. No. 8,338,489.

(60) Provisional application No. 60/989,507, filed on Nov. 21, 2007.

(30) Foreign Application Priority Data

Oct. 19, 2007  (EP) ..................... 07291273

(51) Int. Cl.
| A61K 31/00 | (2006.01) |
| A61K 31/18 | (2006.01) |
| A61K 31/138 | (2006.01) |
| A61K 31/222 | (2006.01) |
| A61K 31/36 | (2006.01) |
| A61K 31/404 | (2006.01) |
| A61K 31/4045 | (2006.01) |
| A61K 31/4704 | (2006.01) |
| A61K 31/5377 | (2006.01) |

(52) U.S. Cl.
CPC .............. *A61K 31/138* (2013.01); *A61K 31/00* (2013.01); *A61K 31/18* (2013.01); *A61K 31/222* (2013.01); *A61K 31/36* (2013.01); *A61K 31/404* (2013.01); *A61K 31/4045* (2013.01); *A61K 31/4704* (2013.01); *A61K 31/5377* (2013.01)

(58) Field of Classification Search
CPC ....... A61K 31/00; A61K 31/18; A61K 31/36; A61K 31/138; A61K 31/222; A61K 31/404; A61K 31/4045; A61K 31/4704; A61K 31/5377
See application file for complete search history.

(56) References Cited

U.S. PATENT DOCUMENTS

| 3,466,325 | A | 9/1969 | Brandstrom et al. |
| 3,501,769 | A | 3/1970 | Crowther et al. |
| 3,655,663 | A | 4/1972 | Wasson |
| 3,657,237 | A | 4/1972 | Weinstock et al. |
| 3,998,790 | A | 12/1976 | Brandstrom et al. |
| 4,034,009 | A | 7/1977 | Zolss et al. |
| 4,252,984 | A | 2/1981 | Manoury et al. |
| 5,116,867 | A | 5/1992 | Klein et al. |
| 5,182,102 | A * | 1/1993 | DeSantis et al. ............. 424/78.1 |
| 6,297,240 | B1 * | 10/2001 | Embleton .................. 514/236.2 |
| 7,459,470 | B2 | 12/2008 | Ernst et al. |
| 8,338,489 | B2 | 12/2012 | Leaute-Labreze et al. |
| 2005/0244458 | A1 * | 11/2005 | Huang et al. ................. 424/426 |
| 2013/0131181 | A1 | 5/2013 | Leaute-Labreze et al. |

FOREIGN PATENT DOCUMENTS

| GB | 1253709 A | 11/1971 |
| GB | 1308106 A | 2/1973 |
| WO | 9740830 A1 | 11/1997 |
| WO | 2006015830 A1 | 2/2006 |
| WO | 2006122007 A1 | 11/2006 |

OTHER PUBLICATIONS

Sozzani et al., The Journal of Biological Chemistry, 1992, The American Society for Biochemistry and Molecular Biology, vol. 267, No. 28, pp. 20481-20488.

Dunzendorfer et. al., Journal of Molecular and Cellular Cardiology, 2000, Academic Press, vol. 32, pp. 915-924.

Akram et al. Iris micrihaemangioma presenting with total hyphaema and elevated intraocular pressure. Eye 2003, 17:784-785.

Baghestanian. The role of beta-adrenergic blockers as antihypertensive medication in patients with peripheral arterial disease. Zeitschrift fur Gefa.beta.medizin 2006, 3(2):11-16 (in German, with English abstract).

Bennett et al. Oral corticosteroid use is effective for cutaneous hemangiomas. An evidence-based evaluation. Arch Dermatol 2001; 137:1208-1213.

(Continued)

*Primary Examiner* — Sarah Pihonak
(74) *Attorney, Agent, or Firm* — Harness, Dickey & Pierce, P.L.C.

(57) ABSTRACT

The present technology relates the use of a beta blocker for the manufacture of a medicament for the treatment of hemangiomas, for example of infantile hemangiomas. The beta blocker may be a non-selective beta-blocker, for example propranolol. The present technology provides an alternative to the known compounds, e.g. corticosteroids, interferon or vincristine, generally used for the treatment of hemangiomas.

16 Claims, 3 Drawing Sheets

(56) References Cited

OTHER PUBLICATIONS

Bielenberg et al. Progressive growth of infantile cutaneous hemangiomas is directly correlated with hyperplasia and angiogenesis of adjacent epidermis and inversely correlated with expression of the endogenous angiogenesis inhibitor, IFN-beta. Int.J. Oncol. 1999; 14:401-408.
Boye et al. Clonality and altered behaviour of endothelial cells from hemangiomas. J Olin Invest 2001; 107:745-52.
Chaturvedi et al. Defining the caspase-containing apoptotic machinery contributing to cornification in human epidermal equivalents. Exp Dermatol. 2006; 15(1):14-22.
Cremer. Propranolol: A milestone in the treatment of problematic hemangiomas? Monatsschrift Fur Kinderheilkunde 2008, 156(10):942-943. (in German, with English abstract).
D'Angelo et al. cAMP-dependant protein kinase inhibits the mitogenic action of vascular endothelial growth factor and fibroblast growth factor in capillary endothelial cells by blocking Raf activation. J Cell Biochem 1997; 67:353-366.
Enjolras et al. Management of alarming hemangiomas in infancy: a review of 25 cases. Pediatrics 1990;85(4):491-8.
Enjolras. Superficial vascular anomalies. EMC-Pediatrie, Editor. Elsevier; 2004; 129-51 (in French, with English abstract).
Ezekowitz et al. Interferon alfa-2a therapy for life-threatening hemangiomas of infancy. New Engl J Med 1992; 326 (22):1456-63.
Frieden et al. Infantile hemangiomas: current knowledge, future directions. Proceedings of a research workshop on infantile hemangiomas. Pediatr Dermatol 2005; 22(5):383-406.
Fritz et al. Effect of beta-blockade on symptomatic dexamethasone-induced hypertrophic obstructive cardiomyopathy in premature infants: three case reports and literature review. J. Perinatol 1998; 18(1):38-44.
Giatromanolaki et al. The HIF-2alpha/VEGF pathway activation in cutaneous capillary haemangiomas. Pathology 2005; 37(2):149-151.
Goodman and Gilman's The Pharmacological Basis of Therapeutics, Eleventh Edition, Chapter 10, pp. 271-295, 2006.
Iaccarino et al. Ischemic neoangiogenesis enhanced by beta2-adrenergic receptors overexpression: a novel role for the endothelial adrenergic system. Circ Res 2005; 97:1182-1189.
Kilian. Hypertension in neonates causes and treatments. J Perinat Neonatal Nurs 2003; 17(1):65-74.
Leaute-Labreze et al. Efficacy of beta-blockers in infantile capillary haemangiomas: The physiopathological significance and the therapeutic consequences. Annales de Dermatologie et de Venereologie 2008, 135(12):860-862. (in French, with Englishtranslation).
Leaute-Labreze et al., Alarming hemangiomas treated with interferon alpha-2b: 7 cases. Ann. Dermatol. Venerol. 1998, 125:174-178 (in French, with English abstract).
Lutgendorf et al., Stress-Related mediators stimulate vascular endothelial growth factor secretion by two ovarian cancer cell lines. Clinical Cancer Research 2003, 9:4514-4521.
Mancini et al. Proliferation and apoptosis within juvenile capillary hemangiomas. Am J Dermatopathol 1996;18:505-14.
Observations by third parties filed on Jan. 27, 2010 in corresponding EP 08838691.7.
Razon et al. Increased apoptosis coincides with onset of involution in infantile hemangioma. Microcirculation 1998; 5:189-195.
Schuller et al., Beta-adrenergic modulation of NNK-induced lung carcinogenesis in hamsters. J. Cancer Res. Clin. Oncol. 2000, 126:624-630.
Shyu et al. Carvedilol prevents cardiac hypertrophy and overexpression of hypoxia-inducible factor-1alpha and vascular endothelial growth factor in pressure-overloaded rat heart. J Biomed Sci. 2005; 12:409-420.
Sommers Smith et al. Beta blockade induces apoptosis in cultured capillary endothelial cells. In Vitro Cell Dev Biol Anim 2002;38:298-304.
Tanner et al. Growing up with a facial hemangioma: parent and child coping and adaptation. Pediatrics. 1998; 101 (3):446-452.

Thaker et al., Chronic stress promotes tumor growth and angiogenesis in a mouse model of ovarian carcinoma. Nature Medicine 2006, 12(8):939-944.
Tortoriello et al. Frequency of recurrence among infants with supraventricular tachycardia and comparison of recurrence rates among those with and without preexcitation and among those with and without response to digoxin and/or propranolol therapy.Am J Cardiol. 2003; 92(9)1045-1049.
Verhoeckx et al. Beta-adrenergic receptor agonists induce the release of granulocyte chemotactic protein-2, oncostatin M, and vascular endothelial growth factor from macrophages. Int Immunopharmacol 2006; 6:1-7.
Villain et al. Low incidence of cardiac events with beta-blocking therapy in children with long QT syndrome. Eur Heart J 2004; 25:1405-1411.
Wassef et al. Vascular tumours and malformations, classification, pathology and imaging. Ann Chir Plast Esth 2006; 51:263-281 (in French, with English translation).
Zhang et al. Inhibition of pancreatic cancer cell proliferation by propranolol occurs through apoptosis induction. Pancreas 2009, 38(1):94-100.
Leaute-Labreze, Christine et al.; "Propranolol for Severe Hemangiomas of Infancy;" The New England Journal of Medicine, XP-002523408, vol. 358, No. 24, Jun. 12, 2008; pp. 2649-2641.
Bonifazi, E. et al.; "Propranolol in Rapidly Growing Hemangiomas;" European Journal of Pediatric Dermatology, XP008105082, vol. 18, No. 3, 2008; pp. 185-192.
Ah-Fat, F. G., et al.; "Recurrent Visual Loss Secondary to an Iris Microhaemangioma;" Eye, XP008089190, vol. 8, No. 3, 1994; p. 357.
Goodfield, M. J. et al.; "The Clinical Presentation of Cutaneous Angiolipomata and the Response to .beta.-Blockade;" Clinical and Experimental Dermatology, XP008089157, vol. 13, No. 3, May 1988; pp. 190-192.
Brem, Harold et al.; "The Combinations of Antiangiogenic Agents to Inhibit Primary Tumor Growth and Metastasis;" Journal of Pediatric Surgery, XP-002473031, vol. 28, No. 10, Oct. 1993; pp. 1253-1257.
Papathanassiu, Adonia E.; "Novel Inhibitors of Angiogensis and Their Mechanism(s) of Action;" From Dissertation Abstr. Int. B, Order No. DA9828828, XP008089194, 59(4), 1998; 158 pages.
Leaute-Labreze, Christine et al.; "Efficacite des Betabloquants Dans Les Hemangiomes Capillaires Infantiles: Signification Physiopathologique Et Consequences Therapeutiques" (Efficacy of beta-blockers in infantile capillary haemangiomas: thephysiopathological significance and therapeutic consequences); Annales De Dermatologie Et De Venereologie, vol. 135, No. 12; XP008105076, Dec. 2008; pp. 860-862.
Cremer H-J; "Auch bei Kindern effektiv? Adjuvante Steroidtherapie bei bakterieller Meningitis" (Propranolol: A milestone in the treatment of problematic hemangiomas?); Monatsschrift Fur Kinderheilkunde, vol. 156, No. 10, 2008; pp. 941-943.
Storch and Hoeger, Propranolol for infantile haemangiomas: insights into the molecular mechanisms of action, British Journal of Dermatology 163:269-274 (2010).
Anderson et al., Membrane Stabilizing, Anti-Oxidative Interactions of Propranolol and Dexpropranolol with Neutrophils, Biochemical Pharmacology 52:341-349 (1996).
Gidaris et al., Use of Propranolol in Infantile Haemangiomas: Report of Five Cases and Review of the Literature, Hippokratia 15(1):81-83 (2011).
Hamm et al., Skin Tumors in Childhood, Deutsches Arzteblatt Internatioanl, 108(20); 347-53 (2011).
Liu et al., The Regulating Effects of Protein Kinase C on the Tone of Guinea-pig Trachea and Human Lobus Bronchi, Journal of Tongji Medical University 18(2):94-96 (1998).
Mackay et al., Targeting the Protein Kinase C Family: Are We There Yet? Nature Reviews 7:554-562 (Jul. 2007).
Martins et al, Chronic Propranolol Treatment Causes Desensitization of the Steriodogenic Response in Testicular Interstitial Cells But Does Not Alter Protein Kinase C, Archives of Andrology 52:215-221 (2006).

(56) References Cited

OTHER PUBLICATIONS

Bramhall et al., Should we treat all haemangiomas with beta-blockers?, Journal of Plastic, Reconstructive & Aesthetic Surgery (2012), 1-2, doi:10.1016/j.bjps.2012.03.008.
Chakkittakandiyil et al., Timolol Maleate 0.5% or 0.1% Gel-Forming Solution for Infantile Hemangiomas: A Retrospective, Multicenter, Cohort Study, Pediatric Dermatology 1-4, 2011, DOI: 10.111/j.1525-1470.2011.01664.x.
Chisholm et al., Beta-Adrenergic receptor expression in vascular tumors, Modern Pathology (2012), 1-6, doi: 10.1038/modpathol.2012.108.
Hadaschik et al., High levels of Beta2-adrenoceptors are expressed in infantile capillary hemangiomas and may mediate the therapeutic effect of propranolol, J Cutan Pathol 2012, 1-3, doi: 10.111/j.1600-0560.2012.01937.x.
Helfand et al., Drug Class Review on Beta Adrenergic Blockers, Final Report, Oregon Health & Science University, Sep. 2007, 1-81.
Phillips et al., A Review of Beta Antagonist Treatment for Infantile Hemangioma, Journal of Drugs in Dermatology, vol. 11, Issue 7, Jul. 2012, 826-829.
Pope et al., Expanding the therapeutic repertoire of infantile haemangiomas: cohort-blinded study of oral nadolol compared with propranolol, British Journal of Dermatology, vol. 168, Issue 1, Jan. 2013, 222-224, DOI: 10.1111/j.1365-2133.2012.11131.x.
Siegfried et al., More on Propranolol for Hemangiomas of Infancy, N Engl J Med 359; 26, Dec. 25, 2008, 2846-2847.
Greenberger et al., Infantile Hemangioma—Mechanism(s) of Drug Action on a Vascular Tumor, Cold Spring Harb Perspect Med 2011;1:a006460 (10 pages).
Haggstrom et al. Patterns of Infantile Hemangiomas: New Clues to Hemangioma Pathogenesis and Embryonic Facial Development. Pediatrics, Mar. 2006;117(3):698-703.
Hasan et al. Steroid therapy of a proliferating hemangioma: histochemical and molecular changes. Pediatrics 2000;105 (1):117-120.
Itinteang et al. Haemogenic endothelium in infantile haemangioma. J Clin Pathol. Nov. 2010;63(11):982-986. Epub Oct. 5, 2010. PubMed PMID: 20924092.
Itinteang et al. Mesenchymal stem cells in infantile haemangioma. J Clin Pathol. Mar. 2011;64(3):232-236. Epub Jan. 17, 2011. PubMed PMID: 21242328.
Itinteang et al. Pharmacologic therapies for infantile hemangioma: is there a rational basis? Plast Reconstr Surg. Aug. 2011;128(2):499-507. PubMed PMID: 21788841.
Itinteang et al. Primitive erythropoiesis in infantile haemangioma. Br J Dermatol. May 2011;164(5):1097-1100. doi:10.1111/j.1365-2133.2010.10187.x. PubMed PMID: 21518328.
Itinteang et al. Primitive mesodermal cells with a neural crest stem cell phenotype predominate proliferating infantile haemangioma. J Clin Pathol. Sep. 2010;63(9):771-776. Epub Aug. 9, 2010. PubMed PMID: 20696686.
Jinnin et al. Recent progress in studies of infantile hemangioma. J Dermatol. 2010;37(4):283-298.
Jinnin et al. Suppressed NFAT-dependent VEGFR1 expression and constitutive VEGFR2 signaling in infantile hemangioma, Nature Medicine 2008;14(11):1236-1246.
Kleinman et al. Hypoxia-Induced Mediators of Stem/Progenitor Cell Trafficking Are Increased in Children With Hemangioma. Arterioscler Thromb Vasc Biol Dec. 2007;27:2664-2670.
Kulke et al. Phase II study of recombinant human endostatin in patients with advanced neuroendocrine tumors. Journal of Clinical Oncology 2006;24(22):3555-3561.
Leaute-Labreze, Certificate of Achievement, ISSVA "Robert Schobinger Award" in recognition of the Best Clinical Paper, 17th International Workshop on Vascular Anomalies, Jun. 24, 2008.
Leonardi-Bee et al. Interventions for infantile haemangiomas (strawberry birthmarks) of the skin. Cochrane Database Syst Rev. May 11, 2011;5:CD006545. Review. PubMed PMID: 21563155.
Lo et al. Current theories on the pathogenesis of infantile hemangioma. Semin Ophthalmol. 2009;24(3):172-177.

Manning, Kinase-Disease Associations, Cell Signaling Technology, Inc. 2007; pp. 1-17 (www.cellsignal.com).
Martiny-Baron et al., Classical PKC isoforms in cancer, Pharmacological Research 2007; 55:477-486.
North et al. A unique microvascular phenotype shared by juvenile hemangiomas and human placenta. Arch Dermatol 2001;137:559-570.
North et al. Are infantile hemangioma of placental origin? Ophthalmology 2002;109(4):633-634.
North et al. GLUT1: A newly discovered immunohistochemical marker for juvenile hemangiomas. Hum Pathol 2000;31 (1):11-22.
O'Reilly et al. Endostatin: an endogenous inhibitor of angiogenesis and tumor growth. Cell 1997;88:277-285.
Pandey et al. Evaluation and management of infantile hemangioma: an overview. Ostomy Wound Management 2008;54(5):16-29.
Price et al., Propranolol vs Corticosteroids for Infantile Hemangiomas—A Multicenter Retrospective Analysis, Arch Dermotol 2011; 147(12):1371-1376.
Propranolol, The Merck Index, Eleventh Edition, 1989, p. 1246, No. 7852.
Ricketts et al. Interferon-Alpha-2a for the Treatment of Complex Hemangiomas of Infancy and Childhood. Annals of Surgery 1994;219(6):605-614.
Ritter et al. Insulin-like growth factor 2 and potential regulators of hemangioma growth and involution identified by large-scale expression analysis. PNAS 2002;99(11):7455-7460.
Roessler et al., Propranolol for proliferating infantile haemangioma is superior to corticosteroid therapy—a retrospective, single centre study, JEADV 2011, Letter to the Editor (2 pages).
Shayan et al. Use of propranolol in treating hemangiomas. Canadian Family Physician 2011;57:302-303.
Walter et al. Somatic mutation of vascular endothelial growth factor receptors in juvenile hemangioma. Genes Chromosomes Cancer Mar. 2002;33(3):295-303.
Wyeth Pharmaceuticals Inc., Inderal.RTM. (propranolol hydrochloride) Tablets, product package insert, Rev Dec. 2007; pp. 1-18 (www.wyeth.com).
Yu et al. Endothelial progenitor cells in infantile hemangioma. Blood, Feb. 2004;103(4):1373-1375.
Yu et al. Mesenchymal Stem Cells and Adipogenesis in Hemangioma Involution. Stem Cells 2006;24:1605-1612.
Yu et al., Genomic Imprinting of IGF2 is Maintained in Infantile Hemangioma despite its High Level of Expression, http://molmed.e-stacks.com, doi: 10.2119/2004-00045.Bischoff (accepted for publication Dec. 28, 2004) (7 pages).
Zheng et al., Effects of angiotensin-converting enzyme inhibitors and Beta-adrenergic blockers on retinal vascular endothelial growth factor expression in rat diabetic retinopathy, Experimental Eye Research 2007; 84:745-752.
Sans et al., Propranolol for Severe Infantile Hemangiomas: Follow-Up Report, Pediatrics 124(3):e423-e431 (Sep. 2009).
Blanchet et al., Management of Infantile Subglottic Hemangioma: Acebutolol or Propranolol?, International Journal of Pediatric Otorhinolaryngology 74:959-961 (2010).
Clinical trials NCT010308 Nadolol (Feb. 2, 2011).
Clinical trials NCT01147601 Topical Timolol 0.5% solution (Feb. 2, 2011).
Cremer, Propranolol in der Behandlung Prolematischer Hamangiome, Kinder- und Jugendarzt 40(7):1-4 (2009).
Fitzgerald, Testing Whether Drugs That Weaken Norepinephrine Signaling Prevent or Treat Various Types of Cancer, Clinical Epidemiology 2:1-3 (2010).
Greenberger et al., A High-Throughput Screen Identifies Rapamycin as a Specific Inhibitor of Hemangioma Stem Cell-Induced Vasculogensis, 18th International Workshop on Vascular Anomalies, Hemangioma Session III, Brussels, Belgium (2010).
Greenberger et al., Corticosteroid Suppresses VEGF—A Production and Blocks Vasculogenic Activity of Infantile Hemangioma-Derived Stem Cells, 18th International Workshop on Vascular Anomalies, Hemangioma Session III, Brussels, Belgium (2010).
Hoeger, Infantile Haemangioma: New Aspects on the Pathogenesis of the Most Common Skin Tumour in Children, British Journal of Dermatology 164:234-235 (2011).

(56) References Cited

OTHER PUBLICATIONS

Itinteang et al., Expression of Components of the Renin-Angiotensin System in Proliferating Infantile Haemangioma May Account for the Propranolol-Induced Accelerated Involution, Journal of Plastic, Reconstructive & Aesthetic Surgery,doi:10.1016/j.bjps.2010.08.039 (2010).

Khan et al., Multipotential Stem Cells Recapitulate Human Infantile Hemangioma in Immunodeficient Mice, Journal of Clinical Investigation 118(7):2592-2599 (2008).

Khunger et al., Dramatic response to topical timolol lotion of a large hemifacial infantile haemangioma associated with PHACE syndrome, British Journal of Dermatology 164(4):886-888 (Apr. 2011); first published online Apr. 4, 2011 DOI:10.1111/j.1365-2133.2010. 10177.x.

Marie et al., Traitment des hemangiomas infantiles palpebraux par Carteolol Collyre [Treatment of Palpebral Infantile Hemangiomas by Carteolol Collyrium], French Society of Dermatology Seminar Les Quatre Saisons de la SFD (Jan. 14, 2010);http://www.sfdermato.com/doc/RESUMES%20SEANCE%20JANVIER%202010.pdf.

Miller, AAD: Questions Remain About Treating Hemangiomas With Propranolol, Skin & Allergy News, http://www.skinandallergynews.com/news/medical-dermatology/single-article- /aad-questions-remain-about-treating-hemangiomas-with-propranolol/463cf409-8a.html (2011).

Mortureux et al., Traitement d'un hemangiome cervicofacial grave par interferon alpha-2b, Arch Pediatr 2:237-240 (1995).

Observations by third parties filed on Feb. 17, 2011 in corresponding EP 08838691.7.

Orfanos, Therapie der Hautkrankheiten, 2. Auflage, Springer Verlag, Chapter 31:717-718 (2002).

Pope et al., Topical Timolol Gel for Infantile Hemangiomas: A Pilot Study, (Reprinted) Arch Dermatol 146(5):564-565 (2010).

Ritter et al., Pathogenesis of Infantile Haemangioma: New Molecular and Cellular Insights, Expert Reviews in Molecular Medicine 9(32):1-19 (2007).

Sudine et al., Hemangiomas: An Overview, Clinical Pediatrics 46(3):206-221 (2007).

Weibel, Propranolol—Un Nouveau Traitement Pour Les Hemangiomas Infantiles [Propranolol—A New Treatment for Haemangiomas of Infancy], Paediatrica 20(2):29-31 (2009).

Algazi et al., Could treatments with beta-blockers be associated with a reduction in cancer risk? Rev Epidermiol Sante Publique 52:53-65, 2004, English abstract considered.

Fredriksson et al., Norepinephrine Induces Vascular Endothelial Growth Factor Gene Expression in Brown Adipocytes through a beta-Adrenoreceptor/cAMP/Protein Kinase A Pathway Involving Src but Independently of Erk1/2, Journal of Biological Chemistry275(18):13802-13811, May 5, 2000.

Smith et al., In Vitro Releases of Propranolol Hydrochloride from Topical Vehicles, American Journal of Pharmaceutical Education 58:306-309. Fall 1994.

Notice of Opposition by InfectoPharm dated Mar. 9, 2012 from corresponding European Patent No. EP2187878B1.

Letter regarding Opposition Procedure dated Mar. 14, 2012 from corresponding European Patent No. EP2187878B1.

Communication of Notice of Opposition—First Information to Patent Proprietor dated Mar. 19, 2012 from corresponding European Patent No. EP2187878B1.

Notice of Further Oppositions to Opponents dated Apr. 27, 2012 from corresponding European Patent No. EP2187878B1.

Communication of Notice of Opposition and Request to File Observations dated Apr. 27, 2012 from corresponding European Patent No. EP2187878B1.

Barnes et al. Evidence by molecular profiling for a placental origin of infantile hemangioma. Proc Natl Acad Sci USA Dec. 27, 2005;102(52):19097-19102.

Barnes et al. The placenta theory and the origin of infantile hemangioma. Lymphat Res Biol. 2007;5:245-255.

Barrio et al. Treatment of hemangiomas of infancy. Dermatologic Therapy 2005;18:151-159.

Bauland et al. The pathogenesis of hemangiomas: a review. Plast Reconstr Surg. 2006;117(2):29e-35e.

Benezra et al. Endostatin's endpoints—Deciphering the endostatin antiangiogenic pathway. Cancer Cell 2004;5:205-206.

Bertrand et al., Propranolol versus Prednisone in the Treatment of Infantile Hemangiomas: A Retrospective Comparative Study, Pediatric Sermatology 2011; 28(6):649-654.

Bischoff. Progenitor cells in infantile hemangioma. J Craniofac Surg. Mar. 2009;20(Suppl 1):695-697.

Boscolo et al. Vasculogenesis in infantile hemangioma. Angiogenesis 2009;12(2):197-207. Epub May 10, 2009. Review. PubMed PMID: 19430954; PubMed Central PMCID: PMC2810616.

Boye et al. Infantile Hemangioma: Challenges, New Insights, and Therapeautic Promise, Journal of Craniofacial Surgery 2009; 20(Suppl 1):678-684.

Calicchio et al. Identification of Signaling Systems in Proliferating and Involuting Phase Infantile Hemangiomas by Genome-Wide Transcriptional Profiling. Am J Pathol May 2009;174(5):1638-1649. E Pub Apr. 6, 2009.

Chang et al. Growth characteristics of infantile hemangiomas: implications for management. Pediatrics. Aug. 2008;122(2)360-367.

Clarke et al., PKC inhibition and diabetic microvascular complications, Best Practice & Research Clinical Endocrinology & Metabolism 2007; 21(4):573-586.

Dadras et al. Infantile hemangiomas are arrested in an early developmental vascular differentiation state. Mod Pathol. Sep. 2004;17(9):1068-1079.

Dash et al., Effect of propranolol on platelet signal transduction, Biochem. J. 1995; 309:99-104.

Dosanjh et al. In vitro characteristics of neonatal hemangioma endothelial cells: similarities and differences between normal neonatal and fetal endothelial cells. Journal of Cutaneous Pathology 2000;27:441-450.

Drolet et al. Characteristics of infantile hemangiomas as clues to pathogenesis: does hypoxia connect the dots? Arch Dermatol. Nov. 2010;146(11):1295-1299. PubMed PMID: 21079070.

Drolet et al. Hemangiomas in children. N Engl J Med 1999;341(3):173-181.

Folkman et al. Inhibition of angiogenesis. Cancer Biology 1992;3:89-96.

Frieden et al. Propranolol for infantile hemangiomas: promise, peril, pathogenesis. Pediatric Dermatology 2009;26(5):642-644.

Frieden, Infantile Hemangioma Research: Looking Backward and Forward, Journal of Investigative Dermatology 2011; 131:2345-2348.

Greenberger et al. Corticosteroid suppression of VEGF-A in infantile hemangioma-derived stem cells. New England Journal of Medicine 2010;362:1005-1013.

\* cited by examiner

USE OF A BETA BLOCKER FOR THE MANUFACTURE OF A MEDICAMENT FOR THE TREATMENT OF HEMANGIOMAS

CROSS-REFERENCE TO RELATED APPLICATIONS

This application is a continuation of U.S. application Ser. No. 12/599,266, filed on May 11, 2010, which is a National Stage Entry of International Application No. PCT/IB2008/002746, filed on Oct. 16, 2008, which claims priority to U.S. Provisional Application No. 60/989,507, filed on Nov. 21, 2007, and EP 07291273.6, filed on Oct. 19, 2007, all of which are incorporated by reference herein.

TECHNICAL FIELD

The present invention relates the use of a beta-blocker for the manufacture of a medicament for the treatment of hemangiomas, for example of infantile hemangiomas. Also disclosed is a method for the treatment of hemangiomas by using the present invention.

INTRODUCTION

In the following text, the bracketed references are listed in the "Reference Listing" after the "Example" part of the specification.

Infantile capillary hemangiomas (IH) Hemangiomas in children are most commonly recognized in the skin and liver. IH Infantile capillary hemangiomas (IH) are the most common soft tissue tumours of infancy, occurring in 4 to 10% of children under 1 year of age as disclosed in Frieden I J et al, "Infantile hemangiomas: current knowledge, future directions, Proceedings of a research workshop on infantile hemangiomas", Pediatr Dermatol 2005; 22:383-406 [1]. IH is made of a complex mixture of cell types including a majority of endothelial cells, associated with pericytes, dendritic cells and mast cells. Endothelial cells derived from proliferating hemangiomas are clonal in origin as disclosed in document [1] and by Bielenberg D. R. et al, "Progressive growth of infantile cutaneous hemangiomas is directly correlated with hyperplasia and angiogenesis of adjacent epidermis and inversely correlated with expression of the endogenous angiogenesis inhibitor", INF-beta. Int. J. Oncol.; 14:401-408 [21], Boye E, et al. Clonality and altered behaviour of endothelial cells from hemangiomas. J Clin Invest 2001; 107:745-52 [9] suggesting that hemangiomas arise from the clonal expansion of an endothelial precursor cell, which might be derived of a haematopoietic stem cell as disclosed in [1]. IH endothelial cells exhibit a distinctive molecular phenotype characterized by immuno-histochemical positivity in document [1]: indoleamine 2,3-dioxygenase (IDO) and LYVE-1 both positive in early phase IH and lost during maturation to a blood vascular phenotype, Glucose transporter 1 (Glut-1), Lewis Y Ag (Le Y), FcRγII, merosin, CCR6, and CD 15.

Regulators of IH growth and involution are still poor understood, but it has been demonstrated that during their growth phase, two major pro-angiogenic factors are involved: basic fibroblast growth factor (bFGF) and vascular endothelial growth factor (VEGF) which are present in situ, but also in blood and urines as disclosed in document [1], and in Mancini A. J. et al, "Proliferation and apoptosis within juvenile capillary hemangiomas", A. m. J. Dermatopathol. 1996; 18:505-514 [11]. In addition, in situ hybridization for the VEGF receptor (VEGF-R) in proliferative IH has shown that VEGF-Rs are evenly spread throughout the hemangioma and not yet assembled into blood vessels. During the growth phase of IH, histological studies have showed that both endothelial and interstitial cells are in proliferative state (MIB1 staining strongly positive) as disclosed in Mancini et al. Proliferation and apoptosis within juvenile capillary hemangiomas, Am J Dermatopathol 1996; 18:505-14, [10] and on the other hand during the involution phase the cells exhibit markers of apoptosis as disclosed in [10] and Razon M. J. et al, "Increased apoptosis coincides with onset of involution in infantile hemangioma", Microcirculation 1998; 5:189-195 [11]. One hypothesis to explain endothelial cell apoptosis in capillary hemangiomas is the expression of ICAM-1 on the cell surface, but an alternative possibility may be the loss of stimulatory factors such as VEGF [1].

The adrenergic system is the major regulator of cardiac and vascular function. Capillary endothelial cells express beta 2-adrenergic receptors as disclosed in D'Angelo G. et al, "cAMP-dependant protein kinase inhibits the mitogenic action of vascular endothelial growth factor and fibroblast growth factor in capillary endothelial cells by blocking Raf activation", J. Cell Biochem. 1997; 67:353-366 [13], which modulate the release of NO, causing endothelium-dependent vasodilatation. In addition, beta-adrenergic receptors belong to the family of G-protein-coupled receptors and when they are activated by adrenergic catecholamines they can promote a series of intracellular signal transduction pathways as disclosed in Iaccarino G, et al. Ischemic neoangiogenesis enhanced by beta2-adrenergic receptors overexpression: a novel role for the endothelial adrenergic system. Circ Res 2005; 97:1182-1189 [12] and [13]. Beta receptor stimulation can induce modifications of signal transduction pathways of angiogenic factors such as VEGF or bFGF as disclosed in [13]. It has been demonstrated that the increase of cAMP levels inhibit VEGF- and bFGF-induced endothelial cell proliferation. Pharmacological or beta-adrenergic receptor-mediated elevations in cAMP block mitogen-induced activation of the MAPK signaling pathway leading to blockade of Raf-1 activity via increased PKA activity [13]. In addition, it has been demonstrated that betablockade can induce apoptosis of cultured capillary endothelial cells as disclosed in Sommers Smith S. K. et al, "Beta blockade induces apoptosis in cultured capillary endothelial cells", In Vitro Cell Dev. Biol. Anim. 2002; 38:298-304 [14].

Despite their benign self-limited course, common IH are rarely responsible during their proliferative phase for local complications such as ulceration or haemorrhage. The so-called alarming HI disclosed for example in Enjolras O. et al. "Management of alarming hemangiomas in infancy: a review of 25 cases", Pediatrics 1990; 85:491-8 [4], can impair vital or sensorial functions especially when present respectively on upper airways and orbital areas. In addition, IH cause at least transient cosmetic disfigurement which trigger psychological morbidity first in parents and later in affected children as disclosed in document [1] and in Tanner J. L. et al, "Growing up with a facial hemangioma: parent and child coping and adaptation, Pediatrics", 1998; 101:446-452 [2].

Systemic or intralesional corticosteroids are used as first line treatments for problematic lesions during the proliferative phase as disclosed in Bennett M L et al, Oral corticosteroid use is effective for cutaneous hemangiomas, An evidence-based evaluation, Arch. Dermatol. 2001; 137:1208-13 [3]. However, even at high dosages (2 to 5 mg/kg of body weight/day), response rates to treatment range from 30 to 60% as disclosed in documents [1], [3] and [4]. Adverse effects are usually transient and limited such as cushingoid facies, irritability, growth suppression, but may cause more concern hypertrophic myocardiopathy.

Other treatment options include interferon alfa-2a and 2b (40 to 50% of complete response with dosing 1-3 mU/m$^2$/day) (millions of units per m$^2$) but a risk of neurotoxicity has been reported in children under 1 year of age, as disclosed in documents [1] and [5]; vincristine is also used for its antimitotic properties as disclosed in document [1] but its well-known downsides are peripheral neuropathy, constipation, and hematologic toxicity. Further, the new anti-angiogenic factors such as avastatin are contra-indicated in young children because of their side effects. Moreover, because most patients receiving treatment are infants or small children, patient tolerance for the known compounds becomes of more paramount importance. Thus, needs exist of alternative, more efficient and less toxic compounds for the treatment of IH, in particular of infantile capillary hemangiomas. The present invention fulfills these and other needs.

SUMMARY

Propranolol is a well tolerated non-selective beta blocker commonly used in young children for cardiologic indications as disclosed by Villain E et al in Low incidence of cardiac events with beta-blocking therapy in children with long QT syndrome, Eur. Heart J. 2004; 25:1405-11 [6], by Fritz K. I. et al, Effect of beta-blockade on symptomatic dexamethasone-induced hypertrophic obstructive cardiomyopathy in premature infants: three case reports and literature review. J Perinatol 1998; 18:38-44 [7], and by Kilian K. in Hypertension in neonates causes and treatments, J. Perinat Neonatal Nurs. 2003; 17:65-74 [8]. But this beta-blocker and beta-blockers in general have never been experimented nor disclosed for a use in the treatment of hemangiomas. The present inventors are the first ones to have experimented and observed that beta-blockers may be very efficient to control the growth of IH and even to treat IH. The observations and experimental results are provided in the present application.

Accordingly, in a first aspect, the present invention provides the use of beta blocker for the manufacture of a medicament for the treatment of hemangiomas. "Beta blocker" refers also herein to beta-receptor blocking agent, beta adrenergic receptor blocking agent, beta blocking agent, beta-blocking agent or beta-adrenergic receptor blocking agent or any other denomination indicating a chemical that inhibits the binding of agonists, natural or artificial, to beta-adrenergic receptors of any type (beta-1, beta-2, beta-3 or others). According to the present invention, the beta blocker may be a non-selective beta blocker, a beta-1-selective beta blocker, a mixture of alpha-1/beta-adrenergic antagonists, a beta-2-selective beta blocker. The beta-blocker may also be a mixture of two or more beta-blockers.

Examples of beta blocker that may be used in the present invention are disclosed in Goodman and Gilman's the pharmacological basis of therapeutics, eleventh edition, chapter 10, pp 271-295, 2006 [19]. Preferably, according to the present invention, when a non-selective beta blocker is used, it may be selected for example from the group comprising alprenolol, bucindolol, carteolol, carvedilol, labetalol, levobunolol, medroxalol, mepindolol, metipranolol, nadolol, oxprenolol, penbutolol, pindolol, propafenone (propafenone is a sodium channel blocking drug that also is a beta-adrenergic receptor antagonist), propranolol, sotalol, timolol or pharmaceutically acceptable salts thereof, A mixture thereof may be used. When a beta-1 selective beta blocker is used according to the present invention, it may be selected for example from the group comprising acebutolol, atenolol, betaxolol, bisoprolol, celiprolol, esmolol, metoprolol, nebivolol. The beta blocker may also have an intrinsic sympathomimetic activity as acebutolol, betaxolol, carteolol, carvedilol, labetalol, oxprenolol, penbutolol, pindolol, propranolol.

Preferably, the beta blocker is propranolol or a pharmaceutically salt thereof, for example L or D-propranolol or a mixture thereof. The mixture may be a mixture of L and D-propranolol, with an amount thereof of 0:1 to 1:0, for example 1:1. Pharmaceutically acceptable salt of the propranolol may be propranolol chlorhydrate or any other preparation of propranolol, whether or not the preparation changes or alters the pharmacokinetic properties or metabolisation of propranolol.

According to the present invention, the medicament may be a medicament for treating infantile capillary hemangiomas. According to the present invention, the medicament may also be a medicament for treating other vascular tumors, for example those selected from the group comprising hemangiomas (i.e. epitheliod hemangioma, sinusoidal hemangioma, spindle cell hemangioma), tufted angioma, hemangioendotheliomas (i.e. kaposiform hemangioendothelioma), hemangioma in the von Hippel-Lindau syndrome, angiofibroma and angiolipoma in Bourneville disease, pyogenic granuloma, angiosarcomas, for example Kaposi's sarcoma, expanding arteriovenous malformations, tumor-associated vascular proliferation. Reference M. Wassef and coll. Vascular tumours and malformations, classification, pathology and imaging. Ann Chir Plast Esth 2006; 51:263-281 [20] discloses anatomopathologic classification of these active proliferation tumors.

The medicament may be in any form that can be administered to a human or an animal. Administration may be carried out directly, i.e. pure or substantially pure, or after mixing of the beta-blocker with a pharmaceutically acceptable carrier and/or medium. According to the present invention, the medicament may be a syrup or an injectable solution. According to the present invention, the medicament may be a medicament for oral administration selected from the group comprising a liquid formulation, an oral effervescent dosage form, an oral powder, a multiparticule system, an orodispersible dosage form.

For example, when the medicament is a medicament for oral administration, it may be in the form of a liquid formulation selected from the group comprising a solution, a syrup, a suspension, an emulsion and oral drops. When the medicament is in the form of an oral effervescent dosage form, it may be in a form selected from the group comprising tablets, granules, powders. When the medicament is the form of an oral powder or a multiparticulate system, it may be in a form selected from the group comprising beads, granules, mini tablets and micro granules. When the medicament is the form of an orodispersible dosage form, it may be in a form selected from the group comprising orodispersible tablets, lyophilised wafers, thin films, a chewable tablet, a tablet and a capsule, a medical chewing gum.

According to the present invention, the medicament may be a medicament for buccal and sublingual routes, for example selected from the group comprising buccal or sublingual tablets, muco adhesive preparation, lozenges, oromucosal drops and sprays. According to the present invention, the medicament may be a medicament for topical-transdermal administration, for example selected from the group comprising ointments, cream, gel, lotion, patch and foam. According to the present invention, the medicament may be a medicament for nasal administration, for example selected from the group comprising nasal drops, nasal spray, nasal powder. According to the present invention, the medicament may be a medicament for rectal administration, for example suppository or hard gelatin capsule. According to the present invention, the medicament may be a medicament for parenteral administration, for example subcutaneous, intramuscular, intravenous administration.

The skilled person in the art understands clearly that the term "form" as used herein refers to the pharmaceutical formulation of the medicament for its practical use. For example, the medicament may be in a form selected from the group comprising an injectable form (for example as Avlocardyl® 5 mg/ml), syrup (for example as Efferalgan® 3%), oral suspension (for example as Efferalgan® 3%), a pellet (for example as Dafalgan® 1 g), powder (for example as Doliprane® 100 mg), granules (for example as Zoltum® 10 mg), spray, transdermal patch (for example as Cordipatch® 5 mg/24 h) or local form (cream, lotion, collyrium) (for example as Dermoval Creme®, as Betneval® lotion and as Chibroxine® collyre respectively). In these examples, the beta blocker, for example on of the above-cited beta blockers, for example propranolol, may be added or may replace the active ingredient(s) of said medicaments.

The pharmaceutically acceptable carrier may be any know pharmaceutically carrier used for the administration of a beta-blocker to a human or to an animal, depending on the subject. For example, this carrier may be selected from the group comprising for example the monométhoxy-polyéthylènegly-col (for example as in Viraferonpeg®) or Liposome (for example as in Ambizome®). The medium may be any know medium used for the administration of a beta-blocker to a human or to an animal. For example, this medium may be selected from the group comprising for example cremophor (for example as in Sandimmun®) or cellulosis (for example as in Avlocardyl® LP160 mg).

The pharmaceutical form of the drug is selected with regard to the human or animal to be treated. For example, for a child or a baby, a syrup or an injection is preferred. Administration may be carried out with a weight graduated pipette.

According to the present invention, the medicament may comprise any pharmaceutically acceptable and efficient dose of the beta-blocker to treat hemangiomas. For example, the medicament may comprise a dose allowing an administration of 1 to 5 mg/kg of body weight per day, for example of 2 to 4 mg/kg of body weight/day.

In a second aspect, the present invention provides a method of treating a subject suffering from hemangiomas is also disclosed. This method comprises the step of administering to said subject a beta-blocker. Hemangiomas and beta-blockers, as well as usable formulations are as defined above.

The administration can be made by using any pharmaceutical way known by the skilled person and useful to administrate a beta-blocker. Examples of administrable forms of medicament are provided above. For example, the administration can be made by direct injection of the beta-blocker. This way of administration, as well as a syrup, is of course preferred for babies. The administration may be defined so as to allow delivery of a pharmaceutically acceptable and efficient dose for the treatment of hemangiomas. For example, the administration may comprise a dose of 1 to 5 mg/kg of body weight per day, for example of 2 to 4 mg/kg of body weight/day. The administration may be carried out with one dose or with a plurality of doses per day.

The inventors of the present application demonstrate clearly experimentally a strong anti-angiogenic effect in infantile capillary hemangiomas (IH) by the use of a beta-blocker. Further searches carried out by the present inventors with regard to hemangioma show that adrenergic beta2 receptors are present at the surface of the endothelial cells of hemangioma (see examples below). This confirms the results obtained with the present invention, provides physiopathological explanations and confirms the mechanism of action of beta-blockers in the frame of the present invention. This confirms also the link between efficiency of propranolol and its activity as beta-blocker. Since the new anti-angiogenic factors of the prior art such as avastatin are contra-indicated in young children because of their side effect, the use of propranolol according to the present invention constitutes a safe alternative to systemic corticosteroids, and even to interferon or vincristine.

Propranolol is a non-selective beta-blocker with weak intrinsic sympathomimetic activity, and its dramatic therapeutic effect on IH could be explained by three mechanisms:
1. a peripheral vasoconstrictor effect inducing cell hypoxia, Propranolol is responsible for peripheral vasoconstriction, and this effect is immediately visible on the IH we have treated.
2. a decreased expression of VEGF and bFGF genes via the down regulation of the Raf/MAPK pathway, or the HIF pathway (Giatromanoloki A, Arvanitidou V, Hatzimichael A, Simopoulos C, Sivridis E. The HIF-2alpha/VEGF pathway activation in cutaneous capillary haemangiomas. Pathology 2005:149-51 [17]) (Shyu K G, Liou J Y, Wang B W, Fang W J, Chang H. Cardiovedilol prevents cardiac hypertrophy and overexpression of hypoxia-inducible factor-1alpha and vascular endothelial growth factor in pressure-overloaded rat heart. J Biomed Sci. 2005; 12:409-420[18]).
3. an apoptosis triggering effect on capillary endothelial cells.

In the experimental results disclosed hereunder, a change in color from intense red to purple, associated with a palpable softening of the lesion was observed on babies presented with an IH. This effect could induce a chronic hypoxia of the hemangioma responsible for an arrest of endothelial cell proliferation. However, in inventor's experimentations, the progressive improvement of IH under propranolol treatment suggests strongly a sustained action on proliferative growth factors.

It is not clear whether in this respect the targets of the treatment are the endothelial cells themselves, or other cells such as interstitial cells or mast cells. The third mechanism possibly involved to explain the involution of IH is an early endothelial cell apoptosis induced by the beta blockade. However the re-growth of the hemangioma in two of the presented cases, when the treatment was stopped during the proliferative phase of the IH, does not support this hypothesis. In addition, in the second case the inventors did not find apoptotic cell markers by immuno-histochemistry using antibodies to cleaved caspases 3 and 8.

Further, the use of beta-blockers is now widespread in neonate or children patients with a good tolerance in cardiac diseases as long QT syndrome as shown in document Villain E. et al, "Low incidence of cardiac events with beta-blocking therapy in children with long QT syndrome", Eur. Heart J. 2004; 25:1405-1411 [6], hypertrophic cardiomyopathie as shown in document Fritz K. I. et al, "Effect of beta-blockade on symptomatic dexamethasone-induced hypertrophic obstructive cardiomyopathy in premature infants: three case reports and literature review", J. Perinatal 1998; 18:38-44 [7], or hypertension as shown in document Kilian K. et al, "Hypertension in neonates causes and treatments", J. Perinat. Neonatal Nurs 2003; 17: 65-74 [8].

This invention is further illustrated by the following examples with regard to the annexed drawings that should not be construed as limiting.

EXAMPLES

Example 1

Figure 1:
FIG. 1 is a picture showing the aspect of a hemangioma after 4 weeks of a prior systemic steroids treatment, before beginning of propranolol treatment.

First Experiments According to the Present Invention

A male baby presented with an IH involving the nasal pyramid. At 2 months of age, systemic steroids were introduced because of dyspnea associated with nasal partition and columella necrosis. After a one-month treatment at 3 mg/kg of body weight/day (mg/kg/day] of prednisolone, the hemangioma was stabilized, but nasal necrosis progressed. Since the infant progressively refused to take prednisolone tablets, we introduced an equivalent dosage of bethamethasone in drops (0.5 mg/kg/day). At 4 months of age, the hemangioma had stopped growing and intra nasal ulcerations had healed. However, the child returned at a control visit with tachycardia at 180 to 200 pulses per minute, associated with a systolic cardiac murmur. A cardiac sonography showed an obstructive hypertrophic myocardiopathy, justifying a decrease of the betamethasone dosage from 3 to 2 mg/kg of body weight/day (mg/kg/day).

We have thus initiated a treatment with a beta-blocker, propranolol (chemical IUPAC name: (2RS)-1-[1-methylethyl)amino]-3(naphtalen-1yloxy)propan-2-ol) at 3 mg/kg/day. Propranolol was administered as a capsule containing commercial propranolol powder. The day after the onset of propranolol treatment the hemangioma changed in color from intense red to purple, and softened. Betamethasone was replaced by prednisolone which was progressively tapered down and stopped 6 weeks after initiation of propranolol.

Despite the decrease of systemic steroids, the IH still continued to improve. At age 5 months ½, when steroids had been stopped, no rebound in size or coloration of the IH could be noted. At 14 months of age, the child was still under propranolol, and the corticosteroid-induced hypertrophic cardiomyopathy had regressed. The IH was completely flat, with the persistence of only skin telangiectasias on a yellow-orange discolored skin background, and sequels of intranasal and columella necrosis.

Example 2

Second Experiment According to the Present Invention

The second infant, a male triplet, born at 30 weeks, presented since birth a plaque-like IH involving the entire right upper limb and the right fronto-parietal and superior eyelid areas. At one month of age a subcutaneous component developed in 3 areas including the superior eyelid, the parotid region and the axillary fold. Because of risk of visual deprivation prednisolone was started at 3 mg/kg/day. However, after 2 weeks of treatment the situation was not under control and we decided to increase prednisolone at 5 mg/kg/day for 2 weeks. Despite this regimen the IH continued to enlarge and at 2 months of age eyelid opening was impossible, the right side of the face being deformed by an enormous tumor as shown in annexed FIG. 1. In addition the axillary fold was occupied by a tumoral IH component measuring clinically 5 cm in diameter.

MRI showed no intra-cerebral anomalies, but revealed that the IH involved extra and intraconal orbital areas and was responsible for exophthalmia. In addition, MRI showed that the parodital IH was in continuity with a compressive intra-cervical component leading to tracheal and oesophageal deviation; the axillary mass measured 26 mm×45 mm×40 mm and extended to the right pulmonary apex. A cardiac sonography showed an increased cardiac output.

Figure 2:
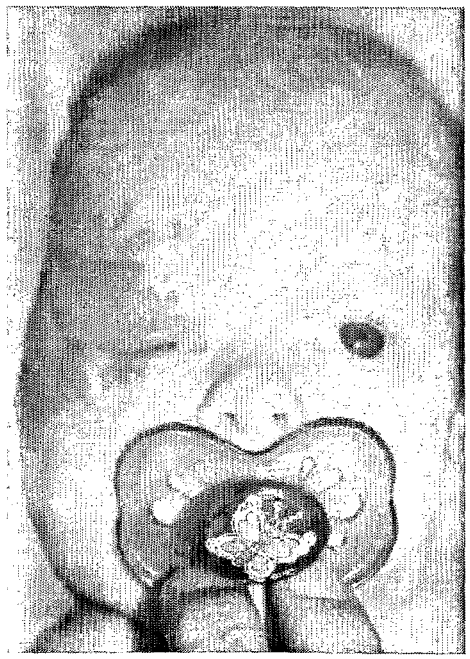
FIG. 2 is a picture showing the aspect of the hemangioma only seven days after onset of propranolol treatment according to the present invention.

The dosage of prednisolone was reduced to 3 mg/kg/day and a treatment with Propranolol, 2 mg/kg/day, according to the present invention, was initiated. Like in the previous infant (see above example 1), the lesions softened only 12 hours after the onset of propranolol. Seven days after, spontaneous ocular opening was possible due to a dramatic reduction in size of the subcutaneous component of the hemangioma as shown in the picture presented in annexed FIG. 2. Parotidal and axillary masses were considerably reduced in size.

These unexpected results obtained with the present invention have to be compared with those presented in the picture of annexed FIG. 1 that shows the aspect of the hemangioma before onset of propranolol treatment and after 4 weeks of a prior art systemic steroids treatment (2 weeks at 3 mg/kg/d and 2 weeks at 5 mg/kg/d). Prednisolone treatment was progressively tapered down while the IH continued to improve. At 3 months of age a biopsy sample was obtained on the arm, showing a typical IH. Endothelial cells demonstrated poor staining with the monoclonal antibody MIB-1 suggesting a weak proliferative activity for an IH in a young infant.

In order to assess a possible proapoptotic role of propranolol, immuno-histochemical analysis using monoclonal anti-cleaved caspase-3 and 8 antibodies (Ozyme, Saint Quentin en Yvelines, France), was performed but did not demonstrate positive immunostaining [15]. Prednisolone was stopped at 4 months of age, without any rebound, but a 3-day interruption of propranolol treatment was responsible for a mild increase in size of the hemangioma on the superior eyelid and parotidal areas. Reintroduction of propranolol treatment at 2 mg/kg/day was successful after only 24 hours.

Figure 3:
FIG. 3 is a picture showing experimental results at 6 months of age where the child still continues to be treated according to the present invention and prior systemic steroids treatment was stopped since 2 months.
Figure 4:
FIG. 4 is a picture showing the experimental results at 9 months of propranolol treatment according to the present invention.

At 6 months of age, the eye opening was satisfactory and no major visual impairment was noted, the parotidal and axillary subcutaneous hemangiomatous components were not palpable and the IH had considerably faded on both face and arm. FIG. 3 provides a picture showing these experimental results at 6 months of age where the child still continue to take 2 mg/kg/d of propranolol but systemic steroids were stopped since 2 months. No subcutaneous component of the hemangioma was noted, and the cutaneous component had considerably faded. In addition the child does not suffered of any visual impairment. At 9 months of age, the treatment was stopped, without any re-growth of the IH as shown in the picture of annexed FIG. 4.

Example 3

Third experimentation according to the present invention

A baby girl presented with a right periocular IH noted first at 3 weeks of age and localized on the internal canthus. At 2 months of age, the subcutaneous component of the IH extended into the orbit and limited the opening of the superior eyelid. Doppler ultrasonography showed an IH measuring 32 mm in diameter and 12 mm in thickness.

After informed consent obtained from the parents, she was treated with propranolol 2 mg/kg/day. Flattening of the lesion was noted in 12 hours, followed by a progressive improvement. Control ultrasonography, performed 7 days after the onset of propranolol, showed a decrease in size of the IH: 21 mm in diameter versus 32 mm and 6 mm in thickness versus 12 mm, without any hemodynamic modifications.

Propranolol was stopped after one month, but a novel increase in size of the IH was noted, necessitating the treatment to be resumed. At 7 months of age the IH was flat and had faded in color, and ultrasonography could not identify any subcutaneous component. Propranolol was stopped at 8 months without any rebound of the hemangioma.

Seven other child suffering from hemangiomas have been treated with propranolol and similar results were obtained. No treatment failure has been observed with the present invention. This kind of results were never achieved in the prior art, for example with corticotherapy or interferon.

In summary, these examples show clearly that propranolol has a strong anti-angiogenic effect in IH. Since the new anti-angiogenic factors such as avastatin are contra-indicated in young children because of their side effects, propranolol, may constitute a reasonable safe alternative to systemic corticosteroids, and even to interferon or vincristine.

Example 4

Comments and Further Experimental Results

The inventors have serendipitously observed that propranolol, well tolerated non-selective beta-blocker commonly used in young children for cardiologic indications, can control the growth phase of IH as reported in Léauté-Labrèze C, Dumas de la Roque E, Hubiche T, Boralevi F, Thambo J B. Propranolol for severe hemangiomas of infancy. New Engl J Med 2008, 358; 24:2650-51 [16]. A possible explanation of the skewed sex ratio, and that the activation of the HIF-2alpha pathway and the subsequent overexpression of VEGF by endothelial cells are involved in the pathogenesis of cutaneous capillary hemangiomas (Giatromanolaki et al, The HIF-2alpha/VEGF pathway activation in cutaneous capillary haemangiomas. Pathology 2005:149-51 [17]). Surprisingly, studying betablockers for the treatment of cardiac hypertrophia, Shyu et al. revealed that cardivedilol reverses both protein and mRNA of HIF-1alpha and VEGF to the baseline values (Shyu et al., Cardiovedilol prevents cardiac hypertrophy and overexpression of hypoxia-inducible factor-1alpha and vascular endothelial growth factor in pressure-overloaded rat heart. J Biomed Sci. 2005; 12:409-420 [18]). Further searches are conduced looking at the angiogenic cascade downstream of beta adrenergic receptors in vivo and in vitro in IH and at possible genetic determinants influencing the HI phenotype.

Histology and Immunohistochemistry

Figure 5:
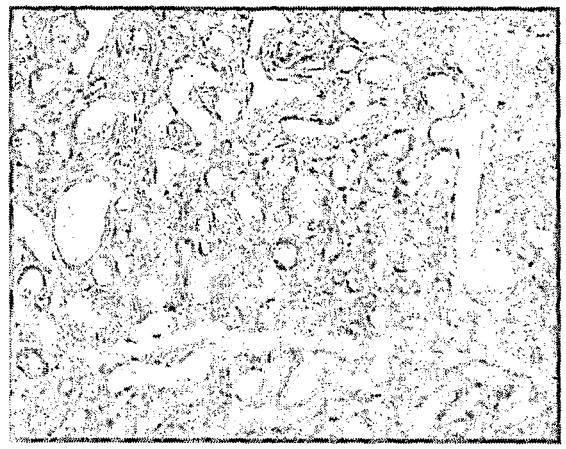
FIG. 5 is a picture obtained with a method of immunohistochemistry showing that beta2 receptors are expressed on endothelial cells of IH.
Figure 6:
FIG. 6 is a picture obtained with a method of immunohistochemistry showing that HIF1 alpha (red staining) are expressed on endothelial cells of IH.

Skin biopsy were embedded in paraffin, cut into 5 μm sections and stained with hematoxylin-eosin to assess the general morphology. To visualize the presence of alpha2-adrenergic receptor and the level of expression of HIF1-alpha, sections were incubated respectively with monoclonal rabbit anti-human alpha2-adrenergic receptor 1:100 (PA1-20659, ABR, Golden, USA) or monoclonal mouse anti-human HIF1-alpha1:1000 (ab8366, abcam, Cambridge, UK) overnight at 4° C. As secondary system, we used Envision horseradish peroxidase system (K4002, K4000 Dako, Trappes, France) which enhances staining sensitivity directed against rabbit for alpha2-adrenergic receptor and mouse for HIF1-alpha. Sections were revealed with aminoethylcarbamide (K3461, Dako, Trappes, France) and counterstained with hematoxylin. Preliminary immunohistochemistry findings showed that beta2 receptors (annexed FIG. 5) are expressed on endothelial cells of IH. HIF1 alpha (annexed FIG. 6) was also expressed on endothelial cells of IH as recently observed.

REFERENCE LISTING

[1] Frieden I J, Haggstrom A, Drolet B A, Mancini A J, Friedlander S F, Boon L, and coll. Infantile hemangiomas: current knowledge, future directions. Proceedings of a research workshop on infantile hemangiomas. Pediatr Dermatol 2005; 22:383-406.

[2] Tanner J L, Dechert M P, B A; Frieden I J. Growing up with a facial hemangioma: parent and child coping and adaptation. Pediatrics. 1998; 101:446-452.

[3] Bennett M L, Fleischer A B, Chamlin S L, Frieden I J. Oral corticosteroid use is effective for cutaneous hemangiomas. An evidence-based evaluation. Arch Dermatol 2001; 137: 1208-13.

[4] Enjolras O, Riche M C, Merland J J, Escande J P. Management of alarming hemangiomas in infancy: a review of 25 cases. Pediatrics 1990; 85:491-8.

[5] Ezekowitz R A B, Phil C B D, Mulliken J B, Folkman J. Interferon alfa-2a therapy for life-threatening hemangiomas of infancy. New Engl J Med 1992; 326:1456-63.

[6] Villain E, Denjoy I, Lupoglazoff J M, Guicheney P, Hainque B, Lucet V, Bonnet D. Low incidence of cardiac events with beta-blocking therapy in children with long QT syndrome. Eur Heart J 2004; 25:1405-11.

[7] Fritz K I, Bhat A M. Effect of beta-blockade on symptomatic dexamethasone-induced hypertrophic obstructive cardiomyopathy in premature infants: three case reports and literature review. J Perinatol 1998; 18:38-44.

[8] Kilian K. Hypertension in neonates causes and treatments. J Perinat Neonatal Nurs 2003; 17:65-74.

[9] Boye E, Yu Y, Paranya G, Paranya G, Mulliken J B, Olsen B R, Bischoff J. Clonality and altered behaviour of endothelial cells from hemangiomas. J Clin Invest 2001; 107: 745-52.

[10] Mancini A J, Smoller B R. Proliferation and apoptosis within juvenile capillary hemangiomas. Am J Dermatopathol 1996; 18:505-14.

[11] Razon M J, Kraling B M, Mulliken J B, Bischoff J. Increased apoptosis coincides with onset of involution in infantile hemangioma. Microcirculation 1998; 5:189-95.

[12] Iaccarino G, Ciccarelli M, Soriento D, Galasso G, Campanile A, Santulli G, Cipolletta E, Cerullo V, Cimini V, Altobelli G G, Piscione F, Priante O, Pastore L, Chiarello M, Salvatore F, Koch W J, Trimarco B. Ischemic neoangiogenesis enhanced by beta2-adrenergic receptors overexpression: a novel role for the endothelial adrenergic system. Circ Res 2005; 97:1182-1189.

[13] D'Angelo G, Lee H, Weiner R I. cAMP-dependant protein kinase inhibits the mitogenic action of vascular endothelial growth factor and fibroblast growth factor in capillary endothelial cells by blocking Raf activation. J Cell Biochem 1997; 67:353-366.
[14] Sommers Smith S K, Smith D M. Beta blockade induces apoptosis in cultured capillary endothelial cells. In Vitro Cell Dev Biol Anim 2002; 38:298-304.
[15] Chaturvedi V, Sitailo L A, Bodner B, Denning M F, Nickoloff B J. Defining the caspase-containing apoptotic machinery contributing to cornification in human epidermal equivalents. Exp Dermatol. 2006 January; 15(1):14-22.
[16] Léauté-Labrèze C, Dumas de la Roque E, Hubiche T, Boralevi F, Thambo J B. Propranolol for severe hemangiomas of infancy. New Engl J Med 2008, 358; 24:2650-51.
[17] Giatromanoloki A, Arvanitidou V, Hatzimichael A, Simopoulos C, Sivridis E. The HIF-2alpha/VEGF pathway activation in cutaneous capillary haemangiomas. Pathology 2005:149-51.
[18] Shyu K G, Liou J Y, Wang B W, Fang W J, Chang H. Cardiovedilol prevents cardiac hypertrophy and overexpression of hypoxia-inducible factor-1alpha and vascular endothelial growth factor in pressure-overloaded rat heart. J Biomed Sci. 2005; 12:409-420.
[19] Goodman and Gilman's the pharmacological basis of therapeutics, eleventh edition, chapter 10, pp 271-295, 2006.
[20] M. Wassef and coll. Vascular tumours and malformations, classification, pathology and imaging. Ann Chir Plast Esth 2006; 51:263-281.
[21] Bielenberg D. R. et al, "Progressive growth of infantile cutaneous hemangiomas is directly correlated with hyperplasia and angiogenesis of adjacent epidermis and inversely correlated with expression of the endogenous angiogenesis inhibitor, INF-beta". Int. J. Oncol.; 14:401-408.

The invention claimed is:

1. A method for treating an infant or small child for an infantile hemangioma, the method comprising administering to the infant or small child a medicament comprising a pharmaceutically acceptable and efficient dose of timolol.

2. The method of claim 1, wherein the medicament is for oral or topical administration.

3. A method for treating a hemangioma comprising administering to a patient in need thereof a pharmaceutically acceptable and efficient dose of timolol, wherein the hemangioma is a capillary hemangioma or capillary infantile hemangioma, and the dose administered per day is less than or equal to 5 mg/kg of body weight of the patient.

4. The method of claim 1, wherein the dose administered per day is less than or equal to 5 mg/kg of body weight of the patient.

5. The method of claim 4, wherein the dose administered per day is from 1 to 5 mg/kg of body weight of the patient.

6. The method of claim 3, wherein the timolol is administered orally in a medicament selected from the group consisting of liquid formulations, oral effervescent dosage forms, oral powders, multiparticule systems, and an orodispersible dosage forms.

7. The method of claim 3, wherein the timolol is administered topically in a medicament selected from the group consisting of ointments, creams, gels, lotions, patches, and foams.

8. The method of claim 3, wherein the timolol is administered in a medicament for nasal, buccal, sublingual, or rectal administration.

9. The method of claim 4, wherein the dose administered per day is from 1 to 5 mg/kg of body weight of the patient.

10. The method of claim 1, wherein the timolol is administered orally in a medicament selected from the group consisting of liquid formulations, oral effervescent dosage forms, oral powders, multiparticule systems, and orodispersible dosage forms.

11. The method of claim 1, wherein the timolol is administered topically in a medicament selected from the group consisting of ointments, creams, gels, lotions, patches, and foams.

12. The method of claim 1, wherein the timolol is administered in a medicament for nasal, buccal, sublingual, or rectal administration.

13. The method of claim 2, wherein the dose administered per day is less than or equal to 5 mg/kg of body weight of the patient.

14. The method of claim 13, wherein the dose administered per day is from 1 to 5 mg/kg of body weight of the patient.

15. The method of claim 2, wherein the timolol is administered orally in a medicament selected from the group consisting of liquid formulations, oral effervescent dosage forms, oral powders, multiparticule systems, and orodispersible dosage forms.

16. The method of claim 2, wherein the timolol is administered topically in a medicament selected from the group consisting of ointments, creams, gels, lotions, patches, and foams.

* * * * *